United States Patent [19]

Hamilton et al.

[11] Patent Number: 5,219,851
[45] Date of Patent: Jun. 15, 1993

[54] TETRAHYDROISOQUINOLINE-TYPE RENIN INHIBITING PEPTIDES

[75] Inventors: Harriet W. Hamilton; William C. Patt, both of Chelsea, Mich.

[73] Assignee: Warner-Lambert Company, Morris Plains, N.J.

[21] Appl. No.: 664,916

[22] Filed: Mar. 5, 1991

[51] Int. Cl.⁵ .................. A61K 31/535; A61K 37/00; C07D 413/00
[52] U.S. Cl. .................. 514/233.5; 514/18; 514/19; 514/913; 514/885; 544/128
[58] Field of Search .............. 514/233.5, 885, 913, 514/18, 19; 544/128

[56] References Cited

U.S. PATENT DOCUMENTS

| | | | |
|---|---|---|---|
| 4,948,793 | 8/1990 | Allison et al. | 514/233.5 |
| 5,063,207 | 11/1991 | Doherty et al. | 514/18 |
| 5,134,123 | 7/1992 | Branca et al. | 514/18 |
| 5,135,914 | 8/1992 | Hamilton et al. | 514/19 |

OTHER PUBLICATIONS

Bolis et al., *J. Med. Chem.*, vol. 30, pp. 1729-1737 (1987).
Plattner et al. *J. Med. Chem.*, vol. 31, No. 12, pp. 2277-2288 (1988).
Denkewalter et al., *Progress in Drug Research*, 1966, vol. 10, pp. 510-512 (1966).
Burger, Medicinal Chemistry, 1960, pp. 565-571, 578-581, 600-601.
Huber et al., *J. Cardiovascular Pharmacology*, 1987, 10 (Suppl. 7), pp. 554-558.

*Primary Examiner*—Ronald W. Griffin
*Attorney, Agent, or Firm*—Elizabeth M. Anderson

[57] ABSTRACT

The invention concerns novel renin-inhibitory compounds which contain a tetrahydroisoquinoline or similar heterocycle at the $P_3$ position. These are useful for treating hypertension, congestive heart failure, glaucoma, hyperaldosteronism, and diseases caused by retroviruses including HTLV-I, -II and -III. Processes for preparing the compounds, compositions containing them, and methods of using them are included. Also included is a diagnostic method which uses the compounds to determine the presence of renin-associated hypertension, or hyperaldosteronism.

17 Claims, No Drawings

TETRAHYDROISOQUINOLINE-TYPE RENIN INHIBITING PEPTIDES

BACKGROUND OF THE INVENTION

Renin is a natural enzyme which is released into the blood from the kidney. It cleaves its natural substrate, angiotensinogen, releasing decapeptide, angiotensin I. This is in turn cleaved by converting enzyme in the lung, kidney and other tissues to an octapeptide, angiotensin II. Angiotensin II raises blood pressure both directly by causing arteriolar constriction and indirectly by stimulating release of the sodium-retaining hormone aldosterone from the adrenal gland causing a rise in extracellular fluid volume. Inhibitors of renin have been sought as agents for control of hypertension, congestive heart failure, and hyperaldosteronism.

U.S. Pat. No. 4,680,284 covers renin inhibiting compounds of the formula:

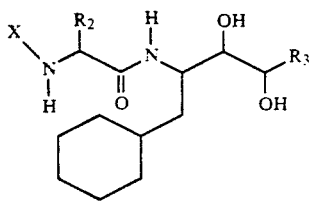

wherein $R_2$ is loweralkyl or arylalkyl; $R_3$ is loweralkyl; X is

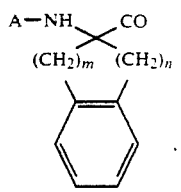

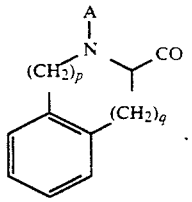

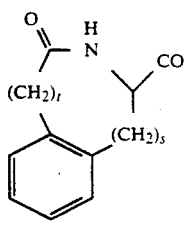

or

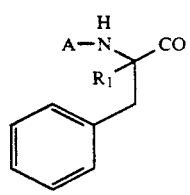

wherein A is hydrogen or an N-protecting group, $R_1$ is loweralkyl or arylalkyl, m is 1-3, n is 1-3, p is 1-3, q is 1-3, s is 1-3, and t is 0-2.

European Application Number EP-229667 covers renin inhibiting peptidyl amino-diols of formula

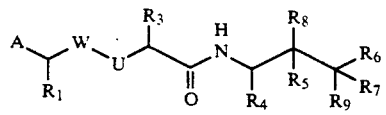

wherein A is a substituent; W is C=O or CHOH; U is $CH_2$ or $NR_2$; $R_1$ is lower alkyl, cycloalkylmethyl, benzyl, 4-methoxybenzyl, halobenzyl, (1-naphthyl)methyl, (2-naphthyl)methyl, (4-imidazoyl)methyl, α,α-dimethylbenzyl, 1-benzyloxyethyl, phenethyl, phenoxy, thiophenoxy or anilino; $R_3$ is lower alkyl, [(alkoxy)alkoxy]alkyl, (thioalkoxy)alkyl, lower alkenyl, benzyl or heterocyclic ring substituted methyl; $R_4$ is lower alkyl, cycloalkylmethyl or benzyl; $R_5$ is vinyl, formyl, hydroxymethyl or hydrogen; $R_7$ is hydrogen or lower alkyl; $R_8$ and $R_9$ are independently selected from OH and $NH_2$; and $R_6$ is hydrogen, lower alkyl, vinyl or arylalkyl.

European Application 186,977 covers certain renin-inhibitory peptides of formula

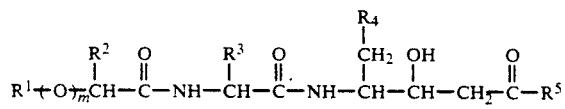

wherein m is 0 or 1 and $R^1$ to $R^3$ are a variety of organic groups. The $R^3$ covers many groups.

A designation for the compounds of this invention is illustrated below. The CAD is considered to occupy the $P_1—P_1'$ positions. For example

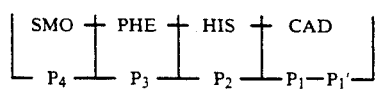

The present invention concerns novel compounds which inhibit renin. It also concerns pharmaceutical compositions containing these novel peptides, methods of treating renin-associated hypertension, congestive heart failure, glaucoma, and hyperaldosteronism, as well as the use of the compounds as diagnostic tools, and the methods for preparing the compounds.

Since HIV protease, like renin, is an aspartyl protease, these compounds can also be used to treat diseases caused by retroviruses including HTLV-I, -II, and -III.

SUMMARY OF THE INVENTION

The present invention relates to novel compounds of the formula

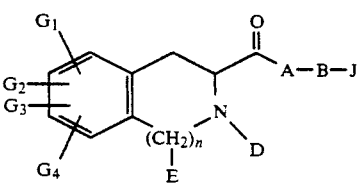

I and the pharmaceutically acceptable acid addition salts thereof wherein A, B, J, D, E, $G_1$, $G_2$, $G_3$, $G_4$ and n are as defined herein below.

The invention also includes pharmaceutical compositions comprising an effective amount of the above compound of formula I in admixture with a pharmaceutically acceptable carrier or excipient and a method for treating renin-associated hypertension in a patient suffering therefrom comprising administering to said patient the above pharmaceutical composition in unit dosage form.

Further the invention includes a pharmaceutical composition comprising an effective amount of a compound of formula I above in admixture with a pharmaceutically acceptable carrier or excipient, and a method for treating hyperaldosteronism in a patient suffering therefrom comprising administering to said patient the above pharmaceutical composition in unit dosage form.

Further the invention includes a pharmaceutical composition comprising an effective amount of a compound of formula I in admixture with a pharmaceutically acceptable carrier or excipient, and a method for treating congestive heart failure in a patient suffering therefrom comprising administering to said patient the above pharmaceutical composition in unit dosage form.

The present invention also includes the use of compounds of formula I to treat diseases caused by retroviruses.

The present invention also includes the use of compounds of formula I above as diagnostic tools for the identification of cases of hypertension due to renin excess.

The present invention further includes a pharmaceutical composition comprising an amount effective for treating glaucoma of a compound of Formula I in admixture with a pharmaceutically acceptable carrier or excipient and a method for treating glaucoma in a patient suffering therefrom comprising administering to said patient the above pharmaceutical composition in unit dosage form.

The invention further includes methods for preparing compounds of formula I above.

DETAILED DESCRIPTION

The following table provides a dictionary of the terms used in the description of the invention.

TABLE I

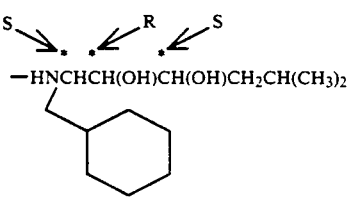

TABLE I-continued

| Abbreviated Designation | |
|---|---|
| TIQ | (tetrahydroisoquinoline structure with C=O and N—S) |
| ALG | (allylglycine structure with NH, C=O, and S) |
| IND | (indoline structure with C=O and NH) |
| BHEAEA | —N—CH₂CH₂—N(CH₂CH₂OH)₂ |

| | Solvents and Reagents |
|---|---|
| $Et_2O$ | Diethyl ether |
| $CHCl_3$ | Chloroform |
| DMF | N,N-Dimethylformamide |
| DMSO | Dimethylsulfoxide |
| HOBT | Hydroxybenzotriazole |
| DCC | N,N'-Dicyclohexylcarbodiimide |
| HOAc | Acetic acid |
| $Et_3N$ | Triethylamine |
| THF | Tetrahydrofuran |
| $CH_2Cl_2$ | Dichloromethane |
| MeOH | Methanol |
| EtOAc | Ethyl acetate |
| DMAP | 4-(N,N-Dimethylamino)-pyridine |

The compounds of the present invention are represented by the formula

I or a pharmaceutically acceptable acid addition salt thereof, wherein

A is ALG, ATM, ATM(K) or GLY wherein K is Z, BOC, TROC or lower alkanoyl;

B is CST, FCS, FCO, CAD or STA;

J is absent when B is CAD or J is OH, $NR_2R_3$ wherein $R_2$ and $R_3$ are each independently hydrogen or a straight or branched lower alkyl or wherein $R_2$ is hydrogen $R_3$ can also be —$(CH_2)_mX$ wherein m is an integer of from 1 to 8 and X is —OH, OR, or (ring structure with Q and N—)

wherein Q is $CH_2$, O, S, or NR and R is as defined below;

D is hydrogen, BOC, Z, (structure: $R_2'$—N($R_3'$)—S(=O)₂—)

wherein Q is as defined above and R, $R_1$, $R_2'$, and $R_3'$ are each independently hydrogen or straight or branched lower alkyl which alkyl is unsubstituted or substituted by one or two hydroxy groups or one or two amino groups.

E is hydrogen or lower alkyl;

$G_1$, $G_2$, $G_3$ and $G_4$ are each independently hydrogen, lower alkyl, lower alkoxy or halogen; and n is an integer of from 0–2.

More preferred compounds of the present invention are those of formula I wherein A is ALG, ATM, ATM(K) or GLY wherein K is Z, BOC, TROC or lower alkanoyl;

B is FCS, FCO, or CAD;

J is absent when B is CAD or J is $NR_2R_3$ wherein $R_2$ and $R_3$ are each independently a straight or branched lower alkyl or $R_2$ is hydrogen and $R_3$ can also be —$(CH_2)_mX$ wherein X is an integer of from 1 to 4 and X is —OH, $OR_4$ or (ring structure with Q and N—)

wherein Q is —$CH_2$—, O, S, or NR;

D is $(R_1O)_2P(=O)—$,  $R_2$—N($R_3$)—S(=O)₂—, or Q(ring)—N—S(=O)₂— wherein Q is as defined above and $R_1$, $R_2$ and $R_3$ are each independently hydrogen or straight or branched lower alkyl which alkyl is unsubstituted or substituted by one or two hydroxy groups or by one or two amino groups;

E is hydrogen;

$G_1$, $G_2$, $G_3$, and $G_4$ are each independently hydrogen, methoxy, methyl or fluorine; and n is 0 or 1.

Still more preferred compounds of the instant invention are those of formula I wherein A is ALG, GLY or ATM;

B is CAD, FCS, or FCO;

J is absent when B is CAD or J is

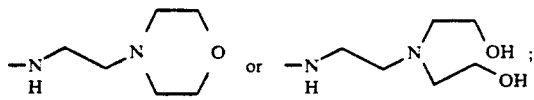

D is

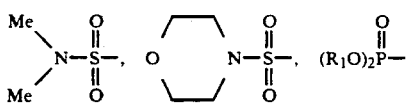

wherein $R_1$ is an alkyl of from 1 to 3 carbons;
E is hydrogen;
$G_1$, $G_2$, $G_3$, and $G_4$ are each hydrogen; and n is one.

Particularly preferred compounds falling within the scope of the invention include the following compounds, their isomers, and pharmaceutically acceptable acid addition salts:

SMO-TIQ-ALG-CAD,
SMO-TIQ-ALG-CST-AEM,
SMO-TIQ-ALG-CST-BHEA,
SMO-TIQ-ALG-FCO-AEM,
SMO-TIQ-ALG-FCS-AEM,
SPI-TIQ-ALG-CAD,
(i-PrO)$_2$PO-TIQ-ALG-CAD,
Z-TIQ-ALG-CAD,
SMO-TIQ-ATM(Z)-CAD,
SMO-TIQ-ATM(TROC)-CAD,
SPI-TIQ-ATM-CAD,
SMO-TIQ-ATM-CAD,
(i-PrO)$_2$PO-TIQ-ATM-CAD,
BOC-TIQ-ATM-CAD,
SMO-TIQ-GLY-CAD,
SMO-TIQ-ATM-CST-AEM,
SMO-TIQ-ATM-FCO-AEM,
SMO-TIQ-ATM-FCS-AEM, and
SMO-IND-ATM-CAD.

The $P_2$ in the present invention may have a substituent K wherein K is Z, BOC, TROC or lower alkanoyl, represented by the abbreviation; ATM(K). The substituent is on the exocyclic nitrogen as shown by

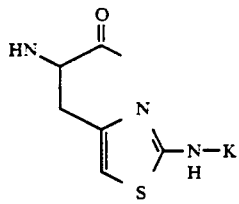

The compounds include solvates and hydrates and pharmaceutically acceptable acid addition salts of the basic compounds of formula I above.

The term pharmaceutically acceptable acid addition salt is intended to mean a relatively nontoxic acid addition salt either from inorganic or organic acids such as, for example, hydrochloric, hydrobromic, hydroiodic, sulfuric, phosphoric, acetic, citric, oxalic, malonic, salicylic, malic, benzoic, gluconic, fumaric, succinic, ascorbic, maleic, tartaric, methanesulfonic, and the like. The salts are prepared by contacting the free base form with a sufficient amount of the desired acid to produce a salt in the conventional manner. The free base forms may be regenerated by treating the salt form with a base.

The compounds of the present invention possess one or more chiral centers and each center may exist in the R(D) or S(L) configuration. The present invention includes all enantiomeric, epimeric and tautomeric forms as well as the appropriate mixtures thereof.

The S isomer at the $P_2$ position is the more preferred.

Some of the above novel compounds may be prepared in accordance with well-known procedures for preparing compounds from their constituent amino acids. Other of the novel compounds of the present invention are prepared by a step-wise procedure or by a fragment coupling procedure depending upon the particular final product desired.

One process for preparing a compound of formula I comprises:

a) reacting an N-protecting amino acid with a desired amine to produce the corresponding amide, b) deprotecting the N protecting group of said amide and coupling it with a desired acid to produce a dipeptidyl like amide, and c) further deprotecting the side chain functions on the amide if necessary to produce the desired compound of formula I and converting, if desired, to a pharmaceutically salt thereof.

An alternate process for preparing a compound of formula I wherein B is FCS or FCO and A is ATM comprises:

a) reacting an ATM amino acid ester with TROC protection on the ATM side chain with an N-protected amino acid to produce a dipeptide ester which is then hydrolyzed to the corresponding dipeptide acid, b) coupling the product of step a) with a $P_1-P_1'$ fragment selected from the group consisting of FCS or FCO to produce the TROC-protected compound of claim 1, and c) deprotecting further, if desired, to produce a compound of claim 1 and converting, if desired, to a pharmaceutically acceptable salt thereof.

The following schemes illustrate novel methods of preparing certain compounds of the present invention.

According to Scheme I below; BOC-ATM(Z), 1, is coupled to CAD, 2, using HOBT/DCC in an inert solvent at 0° C. to 40° C. to give the amide 3. This amide is deprotected using acid, e.g., HCl gas or TFA, in an inert solvent at −10° C. to 40° C. to give the amine, 4. This amine is then in turn coupled to acid 5 using HOBT/DCC in an inert solvent, at 0° C. to 40° C. to give the novel peptoid Example 1. This is then deprotected with H$_2$, Pd/C in a protic solvent to give novel renin inhibitor, Example 2.

SCHEME I

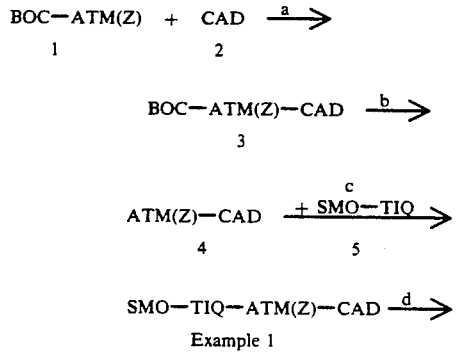

-continued
SCHEME I

SMO—TIQ—ATM—CAD

Example 2

Scheme I can be modified to include the (TROC) protecting group in place of (Z) in order to improve the synthetic route and provide a better method for the preparation of compounds containing FCO and FCS. The TROC protecting group is useful as it is easier to remove in Step d.

SCHEME II

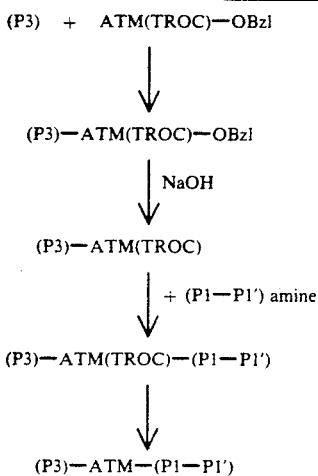

The strategy of peptide chain assembly and selection and removal of protecting groups is discussed in Chapter 1, "The Peptide Bond," in "The Peptides. Analysis, Synthesis, Biology," E. Gross and J. Meienhofer, Eds., Academic Press, New York, N.Y., 1979, Vol. 1, pp. 42–44.

The DCC/HOBT method of coupling is well-known to those skilled in the art and is discussed in Chapter 5, "The Carbodiimide Method" by D. H. Rich and J. Singh in "The Peptides. Analysis, Synthesis, Biology," E. Gross and J. Meienhofer, Eds., Academic Press, New York, N.Y., 1979, Vol. 1, pp. 241–261.

Peptide coupling depends on activating the carboxy terminus of the amino protected amino acid and condensing it with another peptide containing a free amino terminus. In addition to the DCC coupling method described above, other methods of activating the carboxyl group of a protected amino acid include:

1) The azide method—described in Chapter 4 of the above reference.
2) The mixed anhydride method—described in Chapter 6 of the above reference.
3) The active ester method—described in Chapter 3 of the above reference.

The term lower alkyl refers to straight or branched chain alkyl radicals containing from one to six carbon atoms including but not limited to methyl, ethyl, n-propyl, isopropyl, n-butyl, iso-butyl, sec-butyl, 2-methylhexyl, n-pentyl, 1-methylbutyl, 2,2-dimethylbutyl, 2-methylpentyl, 2,2-dimethylpropyl, n-hexyl, and the like.

The term lower alkoxy refers to an alkyl portion of from one to four carbons; preferred is methoxy.

The term lower alkanoyl refers to alkanoyl groups of from one to four carbon atoms.

The term halogen includes fluorine, bromine and chlorine; fluorine is preferred.

The compounds of the present invention are useful for treating renin-associated hypertension, congestive heart failure, hyperaldosteronism, and other related illnesses. They are useful as agents in treating glaucoma. They are also useful as diagnostic tools for determining the presence of renin-associated hypertension or hyperaldosteronism.

Pharmaceutical compositions which comprise an effective amount of the compound in combination with a pharmaceutically acceptable carrier are part of the present invention. An important aspect of the present invention is a method of treating renin-associated hypertension in a mammal which comprises administering a pharmaceutical composition containing an effective amount of a compound of the invention in combination with a pharmaceutically acceptable carrier to the mammal.

Another equally important aspect of the present invention is a method of treating hyperaldosteronism in a mammal which comprises administering a pharmaceutical composition containing an effective amount of a compound of the invention in combination with a pharmaceutically acceptable carrier to the mammal.

An additional aspect of the present invention is a method for treating congestive heart failure in a mammal which comprises administering a pharmaceutical composition containing an effective amount of a compound in combination with a pharmaceutically acceptable carrier to the mammal.

Yet another aspect of the present invention is a process for preparing a compound of formula I according to claim 1.

The effectiveness of the aforementioned compounds is determined by a test for in vitro renin inhibitory activity. This activity is determined by a standard radioimmunoassay for angiotensin I. In this assay the enzyme, renin, incubated for 2 hours at 37° C. in the presence of a substrate, angiotensinogen, generates the product, angiotensin I. Test compounds are added to the incubation mixture. Relative activity is reported as the $IC_{50}$, which is the molar concentration of test compound causing a 50% inhibition of the renin activity.

The compounds of the present invention have the advantages of increased stability toward chymotrypsin hydrolysis, which is described by *J Med Chem*, Vol. 31, No. 2, page 292, 1988. This property makes the compounds more stable in vivo and therefore they exhibit a longer duration of in vivo activity.

Compounds of this invention have also demonstrated in vivo activity represented by lowering blood pressure in conscious monkeys. In vivo effectiveness is determined by their effect on blood pressure in high-renin, unanesthetized, sodium-deplete, normotensive Rhesus or Cynomolgus monkeys.

The following describes this test. Monkeys were acclimated to a low sodium diet and trained to rest quietly in a restraining device. Next, vascular access ports were surgically implanted for intravenous administration of test compounds and direct measurement of blood pressure. At least one week was allowed for recovery from surgery before sodium depletion was accomplished by giving furosemide (1 mg/kg/day, IM) for 4 consecutive days prior to testing. The animals were removed from their home cage and placed in the restraining device. After a 20- to 30-minute acclimation period, a control blood sample (arterial) was taken for determination of plasma renin activity (PRA). Next, either vehicle (absolute ethanol, 0.2 mL/kg) or test compound (5 mg/kg) was infused intravenously over a 10-minute period.

Blood pressure was monitored continuously throughout the entire pre- and post-dose period. Blood samples were taken at the mid-point of the infusion and at 0, 15, 30, and 60 minutes post infusion.

Oral activity was determined using the identical pre-dose treatment and administration of the compounds, in a vehicle of 7.5% DMA/30% Tween 80/62.5% H$_2$O, via oral gavage using a 16 French rectal-colon tube.

The compounds of the present invention also possess the advantage of increased selectivity toward the renin enzyme versus other aspartyl protease enzymes.

TABLE II

In Vitro Renin Inhibition

| Compound | IC50 (or % inhibition at $10^{-6}$M) Renin |
| --- | --- |
| SMO—TIQ—ATM—CAD | 2.7 nm |
| SMO—TIQ—ATM(Z)—CAD | 1% at $10^{-6}$ |
| BOC—TIQ—ALG—CAD | 146 nm |
| BOC—TIQ—GLY—CAD | 11.9% at $10^{-6}$ |
| (i-PrO)$_2$PO—TIQ—GLY—CAD | 19.5% at $10^{-6}$ |
| SMO—TIQ—ALG—CAD | 6.85 |
| SMO—TIQ—GLY—CAD | 1013 nm |

TABLE III

In Vivo Blood Pressure Lowering by Renin Inhibitors

| | | (mm Hg drop in mean B.P.) | | | |
| --- | --- | --- | --- | --- | --- |
| PO Dose | n | 1 | 2 | 4 | 6 |
| 30 mg/kg | 3 | −7 | −15 | −14 | −15 |

As can be seen from the above tables, the compounds of the present invention have a significant effect on the activity of renin and thus are useful for the treatment of hypertension, hyperaldosteronism, and congestive heart failure.

The compounds of the instant invention, when tested by measuring the effect on intraocular pressure in rabbits as described by Tinjum, A. M., *Acta Ophthalmologica* 50, 677 (1972), are expected to inhibit antiglaucoma activity. For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be encapsulating material. In powders, the carrier is a finely divided solid which is in admixture with the finely divided compound. In the tablet the active compound is mixed with carrier having the necessary binding properties in suitable proportions and compacted in the shape and size desired. The powder and tablets preferably contain from 5 to 10 to about 70 percent of the active ingredient. Suitable solid carriers are magnesium carbonate, magnesium stearate, talc, sugar, tragacanth, methylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration. The compound of the present invention may be administered orally, buccally, parenterally, by inhalation spray, rectally, or topically in dosage unit formulations containing conventional nontoxic pharmaceutically acceptable carriers, adjuvants and vehicles as desired. The term parenteral as used herein includes subcutaneous injections, intravenous, intramuscular, intrasternal injection, or infusion techniques.

For preparing suppositories, a low melting wax such as a mixture of fatty acid glycerides or cocoa butter is first melted, and the active ingredient is dispersed homogeneously therein by stirring. The molten homogeneous mixture is then poured into convenient sized molds, allowed to cool, and thereby solidify.

Liquid form preparations include solutions, suspensions, and emulsions. As an example may be mentioned water or water/propylene glycol solutions for parenteral injection. Liquid preparations can also be formulated in solution in aqueous polyethyleneglycol solution. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dosage form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like, as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampules. The unit dosage form can also be a capsule, cachet, or tablet itself, or it can be the appropriate number of any of these in packaged form.

The quantity of active compound in a unit dose of preparation may be varied or adjusted from 1 mg to 500 mg, preferably 5 to 100 mg according to the particular application and the potency of the active ingredient.

The compositions can, if desired, also contain other compatible therapeutic agents.

In therapeutic use as renin inhibitors, the mammalian dosage range for a 70-kg subject is from 1 to 2500 mg per day or preferably 25 to 750 mg per day optionally in divided portions. The dosages, however, per day may be varied depending upon the requirements of the patient, the severity of the condition being treated, and the compound being employed. Determination of the proper dosage for a particular situation is within the skill of the art. Generally, treatment is initiated with small dosages which are less than the optimum dose of the compound. Thereafter the dosage is increased by small increments until the optimum effect under the circumstances is reached. For convenience, the total daily dosage may be divided and administered in portions during the day if desired.

In therapeutic use as an antiglaucoma agent, the compound may also be administered as a topical corneal application of a solution containing the compound in amounts as known to one skilled in the treatment.

The present invention includes combinations of novel renin-inhibiting compounds of formula I with one or more antihypertensive agents selected from the group consisting of diuretics, α- and/or β-adrenergic blocking agents, calcium channel blocking agents, central nervous system-acting agents, adrenergic neuron blocking agents, vasodilators, angiotensin converting enzyme inhibitors, and other antihypertensive agents.

The following examples are provided to enable one skilled in the art to practice the present invention. These examples are not intended in any way to limit the scope of the invention but are illustrative thereof.

EXAMPLE 1

SMO-TIQ-ATM(Z)-CAD

In 25 mL of DMF was dissolved 1.64 g SMO-TIQ and 0.676 g HOBT. To this was added sequentially 1.03 g DCC and 2.73 g ATM(Z)-CAD in 15 mL DMF. The mixture was stirred at room temperature for 96 hours. The mixture was filtered free of insolubles and the filtrate evaporated in vacuo to give an oil. The oil was dissolved in 100 mL of ethyl acetate and washed successively with 1N citric acid, saturated NaHCO₃ and brine (100 mL). The organic phase was then dried over MgSO₄ and evaporated to give a yellow foam. The material was purified by flash chromatography (200 g silica gel, 5% methanol/methylene chloride). The appropriate fractions were combined and evaporated to give 2.6 g of product; mp 98–102° C.; MS; M+856.

Anal.: Calcd: C, 58.78; H, 6.76; N, 9.41. Found: C, 58.99; H, 6.84; N, 9.83.

EXAMPLE 2

SMO-TIQ-ATM-CAD

In 40 mL methanol was dissolved 2.35 g SMO-TIQ-ATM(Z)-CAD, 1.05 g p-tosyl acid and 20% Pd/C. This mixture was stirred at room temperature under a hydrogen atmosphere for 6 hours. The mixture was then filtered free of catalyst and evaporated free of solvent in vacuo. This gave an oil which was dissolved in 100 mL ethyl acetate and washed successively with saturated NaHCO₃ and brine (100 mL). The organic phase was dried over MgSO₄ and evaporated to give a foam. This was purified by flash chromatography (200 g silica gel, 3:1 (ethyl acetate: methylene chloride)). The appropriated fractions were combined to give a 0.85 g product; mp 99–104° C.; MS; M+722.

Anal.: Calcd: C, 56.64; H, 7.27; N, 11.66. Found: C, 56.44; H, 7.36; N, 11.44.

EXAMPLE 3

SMO-TIQ-ALG-CAD

A solution of 0.75 g (1.7 mmol) of BOC-ALG-CAD in 2 mL of MeOH and 50 mL of CH₂Cl₂ was treated with HCl(g) for 10 minutes and then stirred for 2 hours. After concentrating, the residue was taken up in CH₂Cl₂ and concentrated again. The residue was dissolved in 5 mL of DMF and treated with iPr₂NEt until basic. The solution was added to an ice cold solution of 0.55 g (1.7 mmol) of SMO-TIQ, 0.24 g (1.8 mmol) of HOBT.H₂O, and 0.37 g (1.8 mmol) of DCC in 10 mL of DMF. The mixture was stirred in an ice bath for 2 hours and then overnight at room temperature. After filtering, the filtrate was concentrated under high vacuum. The residue was taken up in EtOAc/CHCl₃ and washed with 1N citric acid, brine, saturated NaHCO₃, and brine. Drying over Na₂SO₄ and concentrating, afforded a yellow solid which was purified by chromatography on silica gel (MeOH/CHCl₃, 1:39) to yield 0.53 g of a solid. mp 69–73° C., MS (FAB) 649.3 (m+1).

Anal.: Calcd.: C, 61.08; H, 8.08; N, 8.64 Found: C, 60.76; H, 8.25; N, 8.88.

EXAMPLE 4

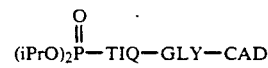

A solution of 0.9 g (1.6 mmol) of BOC-TIQ-GLY-CAD in 50 mL of CH₂Cl₂ and 5 mL of MeOH was treated with HCl(g) for 10 minutes and stirred for 2 hours. After concentrating, the residue was dissolved in CH₂Cl₂ and concentrated again. The residue was dissolved in 2 mL of Et₃N, 3 mL of H₂O, and 2 mL of EtOH. After cooling in an ice bath, the mixture was treated with 0.267 g (1.6 mmol) of diisopropyl phosphite in 2 mL of CCl₄ and stirred overnight at room temperature. The mixture was treated with 1N HCl till pH 1 and extracted with EtOAc (3X). Drying over Na₂SO₄ and concentrating afforded a foam which was purified by chromatography on silica gel (MeOH/CHCl₃, 5% to 7.5%) to yield 0.38 g of a foam; mp 66–77° C., MS (FAB) 624.3 (m+1).

Anal. for C₃₂H₅₄N₃O₇P.H₂O.0.2 CHCl₃: Calcd.: C, 58.10; H, 8.51; N, 6.31; Cl, 3.20. Found: C, 57.98; H, 8.36; N, 6.33; Cl, 3.25.

EXAMPLE 5

SMO-TIQ-GLY-CAD

Dissolved 1.0 g (2.5 mmol) of BOC-GLY-CAD in 2 mL of MeOH and 50 mL of CH₂Cl₂. The solution was treated with HCl(g) for 10 minutes and stirred for 2 hours. After concentrating, the residue was taken up in CH₂Cl₂ and concentrated again. The residue was dissolved in 5 mL of DMF and treated with iPr₂NEt until basic. The solution was added to an ice cold solution of 0.81 g (2.5 mmol) of SMO-TIQ, 0.35 g (2.6 mmol) of HOBT.H₂O, and 0.55 g (2.6 mmol) of DCC in 10 mL of DMF. The mixture was stirred in an ice bath for 2 hours and overnight at room temperature. After filtering, the filtrate was concentrated under high vacuum. The residue was taken up in CHCl₃ and washed with 1N citric acid, brine, saturated NaHCO₃, and brine. Drying over Na₂SO₄ and concentrating gave a foam which was purified by chromatography on silica gel (MeOH/CHCl₃, 1:39 to 1:19) to yield 0.93 g of a foam; mp 77-80° C., MS (FAB) 609.5 (m+1).

Anal. for $C_{30}H_{48}N_4O_7S.0.5CHCl_3$: Calcd.: C, 54.80; H, 7.31; N, 8.38. Found: C, 54.96; H, 7.67; N, 8.35.

EXAMPLE 6
BOC-TIQ-GLY-CAD

A solution of 2.5 g (6.24 mmol) of BOC-GLY-CAD in 100 mL of CH₂Cl₂ and 5 mL of MeOH was treated with HCl(g) for 10 minutes and stirred for 2 hours. After concentrating, the residue was taken up in CH₂Cl₂ and concentrated again. The residue was taken up in 30 mL of DMF and treated with iPr₂NEt till basic. The solution was added to an ice cold solution of 1.73 g (6.24 mmol) of BOC-TIQ, 0.89 g (6.55 mmol) of HOBT.H₂O, and 1.37 g (6.55 mmol) of DCC in 10 mL of DMF. The mixture was stirred in an ice bath for 2 hours and then overnight at room temperature. After filtering, the filtrate was concentrated under high vacuum. The residue was taken up in CHCl₃ and washed with 1N citric acid, brine, saturated NaHCO₃, and brine. Drying over Na₂SO₄ and concentrating afforded a semi-foam which was purified by chromatography on silica gel (MeOH/CH₂Cl₂, 1:39) to give a pink solid. The solid was dissolved in CH₂Cl₂ and concentrated to yield 0.46 g of solid; mp 85-89° C., MS (FAB) 560.2 (m+1).

Anal. for $C_{31}H_{49}N_3O_6.0.5\ H_2O.0.09\ CH_2Cl_2$: Calcd.: C, 64.78; H, 8.78; N, 7.29; Cl, 1.11. Found: C, 64.93; H, 8.67; N, 7.30; Cl, 0.99.

EXAMPLE 7
BOC-TIQ-ALG-CAD

A solution of 0.79 g (1.8 mmol) of BOC-ALG-CAD in 50 mL of CH₂Cl₂ and 5 mL of MeOH was treated with HCl(g) for 10 minutes and stirred for 2 hours. After concentrating, the residue was taken up in CH₂Cl₂ and concentrated again. The residue was dissolved in 15 mL of DMF and treated with iPr₂NEt till basic. The solution was added to an ice cold mixture of 0.5 g (1.8 mmol) of BOC-TIQ, 0.25 g (1.9 mmol) of HOBT.H₂O, and 0.39 g (1.9 mmol) of DCC in 5 mL of DMF. The mixture was stirred in ice for 2 hours and overnight at room temperature. After filtering, the filtrate was concentrated under high vacuum. The residue was taken up in CHCl₃ and washed with 1N citric acid, brine, saturated NaHCO₃, and brine. Drying over Na₂SO₄ and concentrating gave a semi-foam which was purified by chromatography on silica gel (MeOH/CHCl₃, 1.5%). The solid was taken up in CH₂Cl₂ and concentrated to yield 0.4 g of a foam. mp 74-78° C., MS (FAB) 600.2 (m+1).

Anal. for $C_{34}H_{53}N_3O_6.0.07\ CH_2Cl_2$: Calcd.: C, 67.55; H, 8.84; N, 6.94; Cl, 0.82. Found: C, 67.32; H, 8.97; N, 7.32; Cl, 0.88.

INTERMEDIATES FOR EXAMPLES 1-7

A
SMO-TIQ

In 30 mL methanol was stirred 10 g TIQ and 5.13 g tetramethylammonium hydroxide (as a 25% solution in methanol). To this was added 80 mL i-propanol and 80 mL toluene and the mixture evaporated in vacuo to give a thick paste. This residue was treated again with 80 mL i-propanol and 80-mL toluene and evaporated to give a paste. This paste was dissolved in a mix of 120 mL THF and 120 mL of i-propanol. This was treated with 5.2 g SMO-Cl (Annallen der Chemie 624, 25 (1959)) and stirred at room temperature overnight. The solution was then evaporated in vacuo to near dryness and partitioned between 300 mL methylene chloride and 300 mL 1N HCl. The acidic layer was discarded and the organic phase extracted with 1N NaOH (3×150 mL). The base layer was acidified with concentrated HCl solution and extracted with methylene chloride (3×150 mL). These organic phases were washed with brine and dried over MgSO₄. Evaporation of the solvents gave 3.65 g of a yellow oil which solidified upon standing.

B
BOC-ATM-OBZL.HCL

N-BOC-Aspartatic acid, α-benzyl ester (40 g, 0.124 mmol) in EtOAc (1 L) was treated at 0° C. with N-methylmorpholine (13.8 g, 0.136 mmol) and isobutyl chloroformate (18.6 g, 0.136 mmol). The mixture was stirred at 0-10° C. for 3 hours. The mixture was filtered free of precipitate and treated with a solution of diazomethane [(~0.175 mmol) freshly distilled from Diazald® (53 g)] in ether (~500 mL). The mixture was stirred for 16 hours under a N₂ stream. The solution was washed with saturated salt solution (500 mL) and evaporated in vacuo to give the diazoketone as a dark oil. This oil was dissolved in ether (400 mL) and carefully treated with HCl gas. The gas treatment stopped when the pH of the solution reached 2 (wet litmus), approximately 2 to 8 minutes. The solution was then immediately treated with a solution of saturated sodium bicarbonate (600 mL). The organics were washed with saturated salt solution (200 mL) and dried over MgSO₄. The organic phase was evaporated in vacuo to give 44.4 g of the chloroketone as a tan solid. This was dissolved in acetone (225 mL) and treated in portions with thiourea (7.6 g, 0.1 mmol). The solution was stirred at room temperature for 24 hours. The mixture was filtered to collect solid, the solid washed with acetone (2×75 mL) and dried in vacuo to give 20.6 g of product as a white solid, mp 144-146° C. The structure was confirmed by NMR and mass spectroscopy.

C
BOC-ATM(Z)

BOC-ATM-OBZL (5.25 g) was dissolved in a mixture of THF (25 mL), CH₂Cl₂ (35 mL) and saturated NaHCO₃ solution (70 mL). To this was added benzylchloroformate (5.41 g) and the mixture vigorously stirred for 18 hours. The solution was diluted with water (100 mL) and ethyl acetate (150 mL). The organics were separated, washed with water (150 mL), and evaporated at reduced pressure to give an oil, 9.2 g, which was dissolved in EtOH (100 mL) and treated with a solution of potassium hydroxide (2.6 g) in water (20 mL). The mixture was stirred for 3 hours and evaporated to dryness. This was diluted with water (75 mL) and the solution was washed with ether (200 mL). The ethereal solution discarded. The aqueous solution was made acidic (pH=3, wet litmus) with citric acid and extracted with ethyl acetate (2×100 mL). The organic phase dried over MgSO₄ and evaporated in vacuo to give a white foam.

D

BOC-ATM(Z)-CAD

To BOC-(S)ATM(Z)-OBZL (2.06 g) in methanol (35 mL) was added a solution of NaOH (0.6 g) in water (10 mL). The solution was stirred at room temperature for 4 hours and then taken to pH=6 (wet litmus) with 1N HCl. The solution was evaporated in vacuo and dissolved in DMF (20 mL). This solution was treated at 0° C. sequentially with $Et_3N$ (1.51 g), HOBT (0.667 g), DCC (1.03 g), and CAD (1.22 g). The mixture was stirred for 72 hours. The mixture was filtered free of solids and the solvent evaporated in vacuo. The residue from evaporation was dissolved in EtOAc (100 mL) and washed sequentially with saturated sodium bicarbonate (100 mL) and saturated salt solution. The organics were dried over $MgSO_4$ and evaporated in vacuo to give a yellow foam. The foam was chromatographed over silica gel to give the product as a white solid, 1.2 g. The structure was confirmed by NMR and mass spectroscopy.

E

ATM(Z)-CAD.HCl

To BOC-(S)ATM(Z)-CAD (1.1 g) in a mix of $CH_2Cl_2$ (75 mL) and MeOH (15 mL) was added HCl (gas) and the solution stirred at room temperature for 3 hours. The solution was evaporated in vacuo to give the product, which was used without further purification. The structure was confirmed by NMR and mass spectroscopy.

F

BOC-ALG

ALG was prepared according to the procedure described in the *Journal of the American Chemical Society*, Vol. 109, pp. 4649–4659, 1987. A solution of ALG (9.16 g) in a mixture of dioxane (150 mL) and 2N NaOH (70 mL) was treated with di-t-butyldicarbonate (34 g). The mixture was stirred overnight, basified to pH 8.5 with 2N NaOH, diluted with water and extracted with ether. The aqueous solution was acidified with citric acid and extracted twice with ether. The combined ether extracts were washed with brine, dried over $Na_2SO_4$ and concentrated to yield BOC-ALG as a solid. MS (CI, $CH_4$) 216(m+1).

G

BOC-ALG-CAD

An ice cold solution of 3.0 g (14.0 mmol) of BOC-ALG in 50 mL of DMF was treated with 1.98 g (14.6 mmol) of $HOBT.H_2O$, 3.05 g (14.6 mmol) of DCC, and 3.39 g (14.0 mmol) of CAD. The mixture was stirred in ice for two hours and then overnight at room temperature. The mixture was filtered and the filtrate concentrated under high vacuum. The residue was taken up in $CHCl_3$, and washed with 1N citric acid, saturated NaCl, saturated $NaHCO_3$, and saturated NaCl. The solution was dried over $Na_2SO_4$ and concentrated to yield a solid which was purified by chromatography on silica gel ($MeOH/CHCl_3$, 1:19) to yield 6.0 of the product. MS (CI) 441 (m+1).

H

BOC-TIQ

A suspension of 5.0 g (28.2 mmol) of TIQ in 70 mL of dioxane and 30 mL of 1N NaOH was treated with 7.0 g (31.8 mmol) of di-t-butyl dicarbonate and stirred overnight at room temperature. The mixture was treated with 1N NaOH till pH 9 and was washed with $Et_2O$ (2X). The aqueous layer was diluted with 50 mL $H_2O$, treated with conc. HCl till pH 2, and extracted with $Et_2O$ (4X). After drying over $Na_2SO_4$, the solution was concentrated to give an oil which was chromatographed on silica gel ($MeOH/CHCl_3$, 1:19) to yield 8.23 g of the product as a glass. MS (FAB) 278 (m+1).

I

BOC-GLY-CAD

A solution of 2.66 g (15.2 mmol) of BOC-GLY, 2.2 g (15.9 mmol) of $HOBT.H_2O$, 4.25 g (15.2 mmol) of CAD.HCl, and 2.16 mL (15.5 mmol) of $Et_3N$ in 40 mL DMF was cooled in ice and treated with 3.32 g (15.9 mmol) of DCC in 5 mL DMF. After 2 hours at 0° C., the mixture was allowed to cool at room temperature for 24 hours. The mixture was filtered and the filtrate concentrated under high vacuum. The residue was taken up in EtOAc and washed with $H_2O$, 1N citric acid, saturated $NaHCO_3$, and saturated NaCl. Drying and removal of the solvent under reduced pressure gave the crude product. Chromatography on silica gel, eluting with $CHCl_3/MeOH$ (97.5/2.5) gave 6.6 g of the product. The structure was confirmed by NMR and mass spectroscopy.

We claim:

1. A compound of the formula

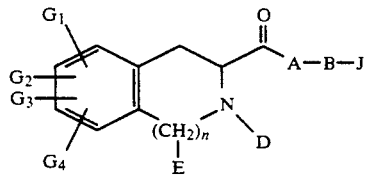

or a pharmaceutically acceptable acid addition salt thereof, wherein

A is ALG, ATM, ATM(K) or GLY wherein K is BOC, TROC, lower alkanoyl or benzyloxycarbonyl;

B is CST, FCS, FCO, CAD or STA;

J is absent when B is CAD or J is OH, $NR_2R_3$ wherein $R_2$ and $R_3$ are each independently hydrogen or a straight or branched lower alkyl or wherein $R_2$ is hydrogen $R_3$ is $—(CH_2)_mX$ wherein m is an integer of from 1 to 8 and X is —OH, OR, or

wherein Q is $CH_2$, O, S, or NR and R is as defined below;

D is hydrogen, BOC, benzyloxycarbonyl,

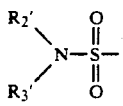

wherein Q is as defined above and R, $R_1$, $R_2'$, and $R_3'$ are each independently hydrogen or straight or branched lower alkyl which alkyl is unsubstituted or substituted by one or two hydroxy groups or one or two amino groups;
E is hydrogen or lower alkyl;
$G_1$, $G_2$, $G_3$ and $G_4$ are each independently hydrogen, lower alkyl, lower alkoxy or halogen; and
n is an integer of from 0 to 2.

2. A compound according to claim 1 wherein
A is ALG, ATM, ATM(K) or GLY wherein K is Z, BOC, TROC or lower alkanoyl;
B is FCS, FCO, or CAD;
J is absent when B is CAD or J is $NR_2R_3$ wherein $R_2$ and $R_3$ are each independently a straight or branched lower alkyl or $R_2$ is hydrogen and $R_3$ is $-(CH_2)_mX$ wherein m is an integer of from 1 to 4 and X is —OH, OR or

wherein Q is $-CH_2-$, O, S, or NR;
D is

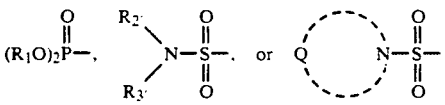

wherein Q is as defined above and $R_1$, $R_2'$ and $R_3'$ are each independently hydrogen or straight or branched lower alkyl which alkyl is unsubstituted or substituted by one or two hydroxy groups or by one or two amino groups;
E is hydrogen;
$G_1$, $G_2$, $G_3$, and $G_4$ are each independently hydrogen, methoxy, methyl or fluorine; and n is 0 or 1.

3. A compound according to claim 1 wherein
A is ALG, GLY or ATM;
B is CAD, FCS, or FCO;
J is absent when B is CAD or J is

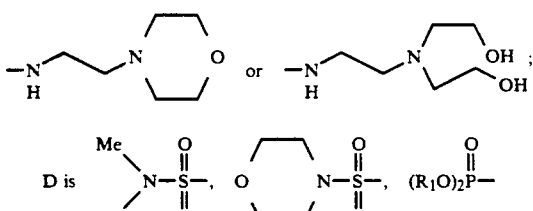

wherein $R_1$ is an alkyl of from 1 to 3 carbons;
E is hydrogen;
$G_1$, $G_2$, $G_3$, and $G_4$ are each hydrogen; and n is one.

4. A compound according to claim 1 selected from:
SMO-TIQ-ALG-CAD,
SMO-TIQ-ALG-CST-AEM,
SMO-TIQ-ALG-CST-BHEA,
SMO-TIQ-ALG-FCO-AEM,
SMO-TIQ-ALG-FCS-AEM,
SPI-TIQ-ALG-CAD,
(i-PrO)$_2$PO-TIQ-ALG-CAD,
Z-TIQ-ALG-CAD,
SMO-TIQ-ATM(Z)-CAD,
SMO-TIQ-ATM(TROC)-CAD,
SPI-TIQ-ATM-CAD,
(i-PrO)$_2$PO-TIQ-ATM-CAD,
BOC-TIQ-ATM-CAD,
SMO-TIQ-GLY-CAD,
SMO-TIQ-ATM-CST-AEM,
SMO-TIQ-ATM-FCO-AEM,
SMO-TIQ-ATM-FCS-AEM, and
SMO-IND-ATM-CAD.

5. A compound according to claim 1 named SMO-TIQ-ATM-CAD.

6. A pharmaceutical composition comprising a renin-inhibitory effective amount of a compound as claimed in claim 1 together with a pharmaceutically acceptable carrier.

7. A pharmaceutical composition according to claim 6 comprising a renin-inhibitory effective amount of a compound named SMO-TIQ-ATM-CAD together with a pharmaceutically acceptable carrier.

8. A pharmaceutical composition comprising a hyperaldosteronism-inhibitory effective amount of a compound as claimed in claim 1 together with a pharmaceutically acceptable carrier.

9. A pharmaceutical composition according to claim 8 comprising a hyperaldosteronism-inhibitory effective amount of a compound named SMO-TIQ-ATM-CAD together with a pharmaceutically acceptable carrier.

10. A pharmaceutical composition comprising an amount effective for treating congestive heart failure of a compound as claimed in claim 1 together with a pharmaceutically acceptable carrier.

11. A pharmaceutical composition according to claim 10 comprising an amount effective for treating congestive heart failure of a compound named SMO-TIQ-ATM-CAD together with a pharmaceutically acceptable carrier.

12. A pharmaceutical composition comprising an amount effective for treating glaucoma of a compound as claimed in claim 1 together with a pharmaceutically acceptable carrier.

13. A pharmaceutical composition according to claim 12 comprising an amount effective for treating glaucoma of a compound named SMO-TIQ-ATM-CAD together with a pharmaceutically acceptable carrier.

14. A pharmaceutical composition comprising an amount therapeutically effective for treating diseases caused by retroviruses including HTLV-I, -II, -III of a compound as claimed in claim 1 together with a pharmaceutically acceptable carrier.

15. A pharmaceutical composition according to claim 14 comprising an amount therapeutically effective for treating diseases caused by retroviruses including HTLV-I, -II, -III of a compound named SMO-TIQ-ATM-CAD together with a pharmaceutically acceptable carrier.

16. A method of determining the presence of renin-associated hypertension in a patient, comprising administering to such a patient, at a hypotensive dosage level and as a single dose, a compound according to claim 1, followed by monitoring of said patient's blood pressure.

17. A method according to claim 16 of determining the presence of renin-associated hypertension in a patient, comprising administering to such a patient, at a hypotensive dosage level and as a single dose, a compound named SMO-TIQ-ATM-CAD followed by monitoring of said patient's blood pressure.

* * * * *

UNITED STATES PATENT AND TRADEMARK OFFICE
CERTIFICATE OF CORRECTION

PATENT NO.   : 5,219,851
DATED        : June 15, 1993
INVENTOR(S)  : Harriet W. Hamilton, et al It is certified that error appears in the above-indentified patent and that said Letters Patent is hereby corrected as shown below:

In Column 18, line 68, after "benzyloxycarbonyl" insert

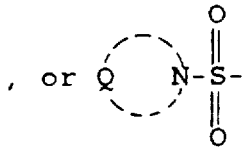

,

In Column 19, line 3 after the structure insert

Signed and Sealed this

Eighth Day of February, 1994

Attest:

BRUCE LEHMAN

*Attesting Officer*      Commissioner of Patents and Trademarks